US007388662B2

(12) United States Patent
Cantin et al.

(10) Patent No.: US 7,388,662 B2
(45) Date of Patent: Jun. 17, 2008

(54) REAL-TIME MEASURING OF THE SPATIAL DISTRIBUTION OF SPRAYED AEROSOL PARTICLES

(75) Inventors: Daniel Cantin, Sainte-Foy (CA); François Babin, Charlesbourg (CA); Marc Lévesque, St-Augustin-de-Desmaures (CA)

(73) Assignee: Institut National D'Optique, Quebec (CA)

( * ) Notice: Subject to any disclaimer, the term of this patent is extended or adjusted under 35 U.S.C. 154(b) by 68 days.

(21) Appl. No.: 11/241,634

(22) Filed: Sep. 30, 2005

(65) Prior Publication Data

US 2007/0076202 A1   Apr. 5, 2007

(51) Int. Cl.
*G01N 15/02* (2006.01)
(52) U.S. Cl. .................................................. 356/338
(58) Field of Classification Search ........ 356/335–343, 356/437, 301; 250/559.08; 701/50, 23; 342/357.13
See application file for complete search history.

(56) References Cited

U.S. PATENT DOCUMENTS

| | | | |
|---|---|---|---|
| 5,116,124 A | 5/1992 | Huttmann | |
| 5,241,315 A | 8/1993 | Spinhirne | |
| 5,278,423 A * | 1/1994 | Wangler et al. | 250/559.4 |
| 5,546,183 A * | 8/1996 | Fegley et al. | 356/336 |
| 5,684,476 A * | 11/1997 | Anderson | 340/988 |
| 5,880,836 A | 3/1999 | Lonnqvist | |
| 6,066,295 A * | 5/2000 | Bernstein et al. | 422/50 |
| 6,199,000 B1 * | 3/2001 | Keller et al. | 701/50 |
| 6,216,071 B1 * | 4/2001 | Motz | 701/50 |
| 6,445,983 B1 * | 9/2002 | Dickson et al. | 701/23 |
| 6,608,677 B1 * | 8/2003 | Ray et al. | 356/301 |
| 6,686,878 B1 * | 2/2004 | Lange | 342/357.13 |
| 6,726,120 B2 * | 4/2004 | Schaffter et al. | 239/69 |
| 6,810,315 B2 * | 10/2004 | Cessac | 701/50 |
| 6,819,265 B2 | 11/2004 | Jamieson et al. | |
| 6,856,396 B2 * | 2/2005 | McGuire | 356/450 |
| 6,862,083 B1 * | 3/2005 | McConnell et al. | 356/4.01 |
| 6,876,920 B1 * | 4/2005 | Mailer | 701/207 |
| 6,926,211 B2 * | 8/2005 | Bryan et al. | 239/311 |
| 2002/0118352 A1 * | 8/2002 | Ohzu et al. | 356/5.04 |
| 2003/0016350 A1 * | 1/2003 | Cheng et al. | 356/301 |

OTHER PUBLICATIONS

Ishizawa et al., "Semiquantitative at-line measurement system for multiresidues of pesticide in food based on the ATR spectroscopy", IEEE Instrumentation and Measurement Technology Conference (1998), p. 678.*

(Continued)

*Primary Examiner*—Tarifur Chowdhury
*Assistant Examiner*—Jonathan M Hansen
(74) *Attorney, Agent, or Firm*—Merchant & Gould P.C.

(57) ABSTRACT

An optical system for measuring in real-time the spatial distribution of aerosol particles, such as pesticides or the like, sprayed from a vehicle over an agricultural field. An optical sensor is mounted directly on the vehicle and sends an excitation light beam through the aerosol as it is being sprayed. The resulting scattered light is received and analyzed to deduce therefrom information on the spatial distribution of the particles. This information is relayed to a processing unit, which in turn provides spraying instructions, for example a warning signal, to the operator of the system. The spraying of the aerosol can therefore be controlled in real-time to avoid contamination of sensitive areas.

30 Claims, 5 Drawing Sheets

OTHER PUBLICATIONS

Stoughton et al., "A comparison of spray drift predictions to lidar data", Agricultural and Forest Meteorology (1997), pp. 15-26.*

Hardesty et al., "Estimation of wind velocity and backscatter signal intensity from Doppler lidar returns", Signals, Systems and Computers, 1997., Nov. 1997, vol. 1, pp. 269-273.*

Miller et al., "Remote Measurement of Spray Drift from Orchard Sprayers Using LIDAR", 2003 ASAE Annual International Meeting, Paper No. 031093.

Walklate et al., "Comparison of Different Spray Volume Deposition Models Using LIDAR Measurments of Apple Orchards", Biosystems Engineering (2002); 82(3): 253-267.

Chourdakis, Giorgos et al., "Analysis of the receiver response for a noncoaxial lidar system with fiber-optic output", Applied Optics, May 20, 2002, vol. 41, No. 15, pp. 2715-2723.

Halldorsson, T. et al., "Geometrical form factors for the lidar function", Applied Optics, vol. 17, No. 2, Jan. 15, 1978, pp. 240-244.

Harms, J. et al., "Geometrical compression of lidar return signals", Applied Optics, Apr. 1, 1978, vol. 17, No. 7, pp. 1131-1135.

Harms, J., "Lidar return signals for coaxial and noncoaxial systems with central obstruction", Applied Optics, May 15, 1979, vol. 18, No. 10, 1559-1566.

Stute, Uwe et al., "Aspects of temporal and spatial ranging for bistatic submarine lidar", Proceedings of EARSeL-SIG-Workshop LIDAR, Dresden/FRG, Jun. 16-17, 2000, 96-105.

Velotta, Raffaele et al., "Analysis of the receiver response in lidar measurements", Applied Optics, Oct. 20, 1998, vol. 37, No. 30, pp. 6999-7007.

\* cited by examiner

REAL-TIME MEASURING OF THE SPATIAL DISTRIBUTION OF SPRAYED AEROSOL PARTICLES

FIELD OF THE INVENTION

The present invention relates to the field of applied optics, and more particularly concerns the use of an optical sensing system for detecting the drift of aerosol particles and controlling the spraying thereof, especially in an agricultural context.

BACKGROUND OF THE INVENTION

It is a common agricultural practice to spray products in aerosol form, such as pesticides, over agricultural fields to improve culture of crops of various types. One major problem with this practice is the lack of control over, and knowledge of, the final destination of the sprayed aerosol. The cloud of sprayed particles are easily carried away from the immediate vicinity of the sprayer by winds, and may land in is locations where they are damageable to the environment or the population, such as nearby streams, fields, residential areas, etc. Traditionally, qualified personnel rely on weather information, in particular wind direction and velocity, in order to estimate where the sprayed particles will go, but this technique lacks precision and there is no way to quickly verify if the operator's assumptions are correct.

One partial solution to this problem using optical technology has been proposed in U.S. Pat. No. 6,862,083 (McCONNELL Sr. et al). McCONNELL suggests the use of a rangefinder, an optical sensor using a pulsed laser beam to measure the distance of solid objects. The rangefinder can detect the presence of trees and classify them according to height, width and tree foliage volume. This information is used to map an orchard or grove and determine what amount of chemical products such as pesticides or the like should be applied to each tree. This system is not however appropriate for crops where solid objects cannot be found. In addition, it does not take into consideration the drift of the aerosol particles when applied.

Research in recent years has demonstrated that control of sprayed pesticides requires the direct measurement of the progression of the sprayed aerosol particles, not a measurement of surrounding vegetation. It is known, in the context of such research, to use traditional long-range LIDAR systems for measuring the drift of pesticides over a field. For example, in the publication by Miller D. R. et al entitled "Remote measurement of spray drift from orchard sprayers using LIDAR"(ASAE paper n. 031093 St-Joseph Mich. 2003), there is shown such a use where the long-range, expensive LIDAR sensor is positioned at one corner of a field and scanned over this field as the pesticide is sprayed. Although this document and other similar research provide valuable information on the parameters influencing the drift of pesticides and their effect on the environment, they do not provide a solution to the control of day-to-day spraying operations.

There is therefore a need for a system allowing the real-time measurement and control of the drift of aerosol particles sprayed over a field.

SUMMARY OF THE INVENTION

Accordingly, the present invention provides an optical system for measuring in real-time the spatial distribution of particles in an aerosol, the aerosol being sprayed from a sprayer mounted on a vehicle operated by an operator.

The optical system first includes an optical sensor having a light source assembly projecting an excitation light beam through the aerosol jointly to the spraying thereof. The excitation light beam is scattered by the particles, thereby producing scattered light. The optical sensor further includes a detecting assembly for detecting part of the scattered light and obtain therefrom information on the spatial distribution of the particles. Mounting means for mounting the optical sensor on the vehicle are also provided.

The optical system according to the invention further includes a processing unit in communication with the optical sensor for receiving therefrom the information on the spatial distribution of the particles. The processing unit provides spraying instructions based on this information to the operator in real-time.

According to another aspect of the invention, there is also provided an agricultural spraying system for the controlled spraying of aerosol particles over a delimited area.

The agricultural system according to this aspect of the invention includes a vehicle for circulating over the delimited area, the vehicle being operated by an operator. A sprayer is mounted on this vehicle for spraying the aerosol particles as the vehicle circulates over the delimited area.

The agricultural system further includes an optical system for measuring in real-time a spatial distribution of the particles. The optical system first includes an is optical sensor having a light source assembly projecting an excitation light beam through the aerosol jointly to the spraying thereof. The excitation light beam is scattered by the particles, thereby producing scattered light. The optical sensor further includes a detecting assembly for detecting part of the scattered light and obtain therefrom information on the spatial distribution of the particles. Mounting means for mounting the optical sensor on the vehicle are also provided. The optical system further includes a processing unit in communication with the optical sensor for receiving therefrom the information on the spatial distribution of the particles. The processing unit provides spraying instructions based on this information to the operator in real-time.

Various aspects and advantages of the present invention will be better understood upon reading of preferred embodiments thereof with reference to the appended drawings.

DESCRIPTION OF PREFERRED EMBODIMENTS OF THE INVENTION

Figure 1:
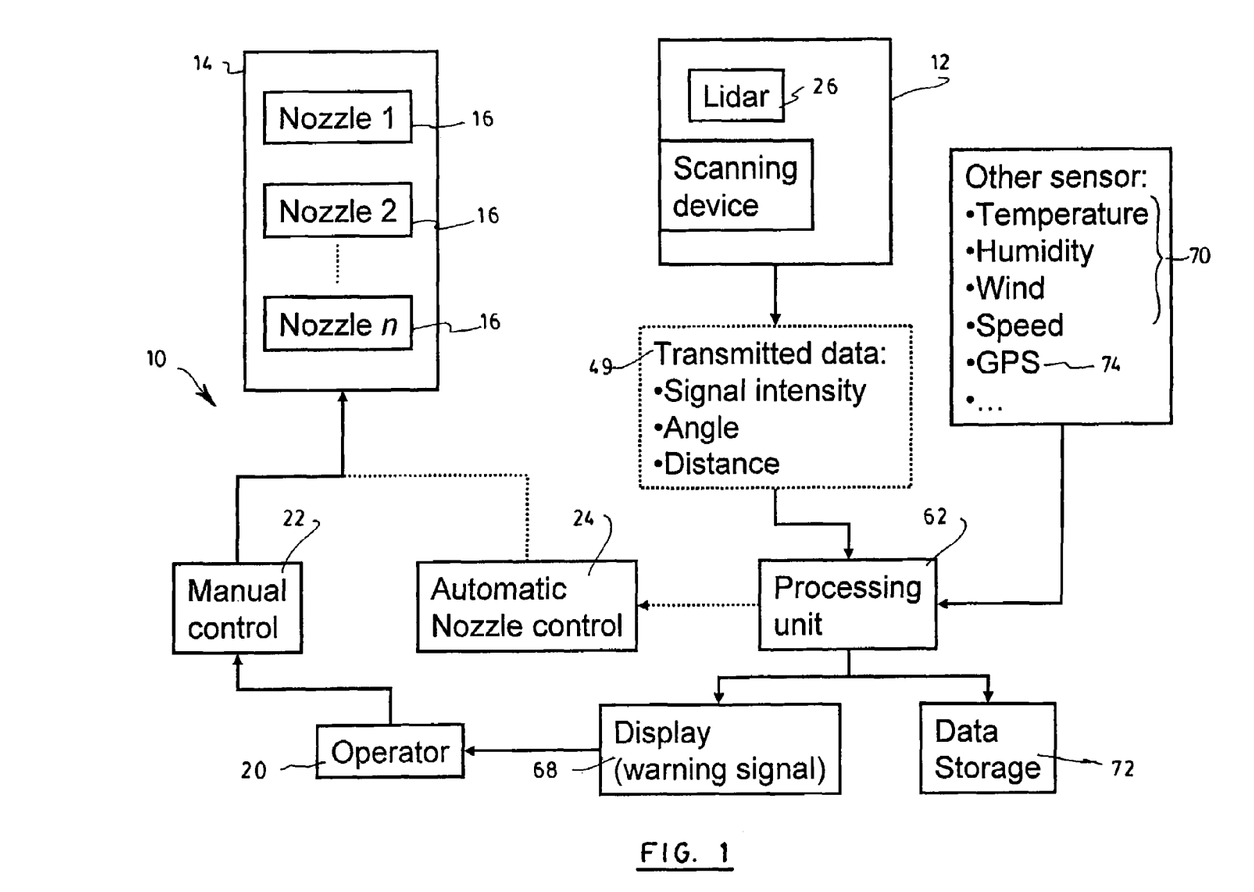
FIG. 1 is a block diagram of an agricultural spraying system according to one embodiment of the present invention.
Figure 2:
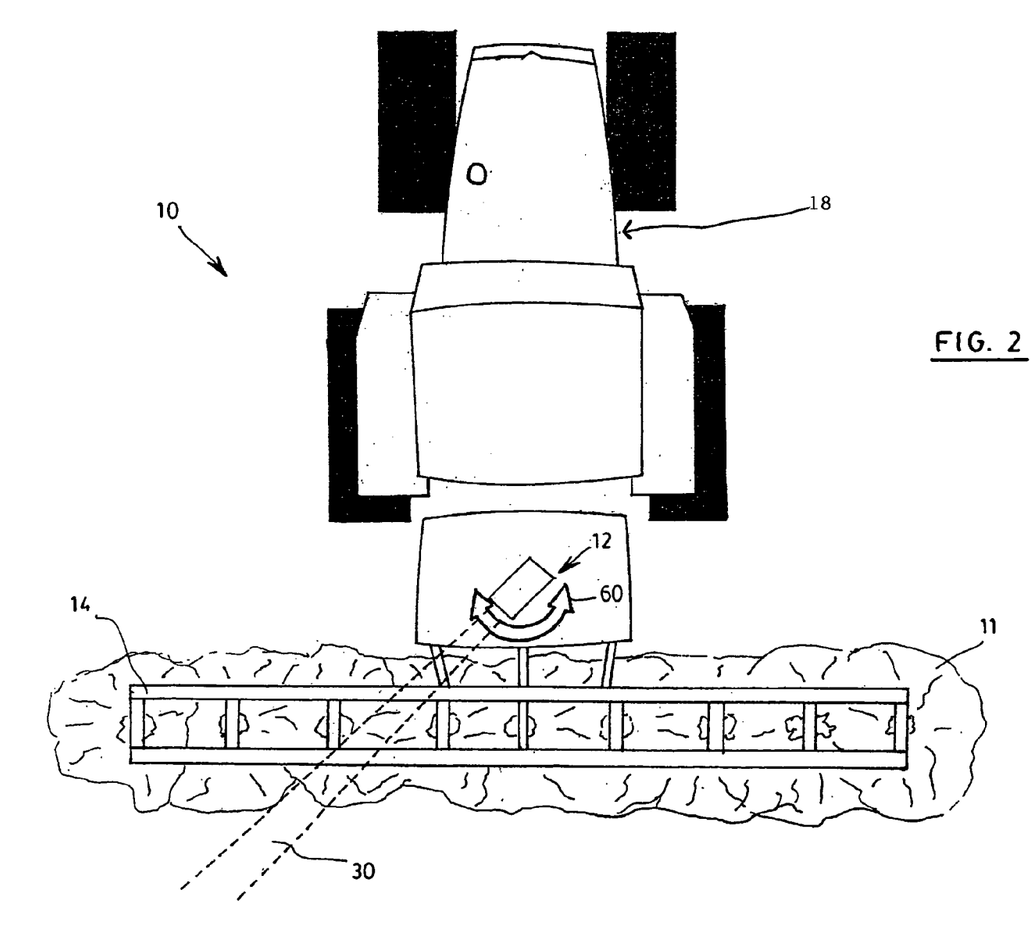
FIG. 2 is a top view of a tractor provided with an optical system according to a preferred embodiment of the invention.
Figure 3:
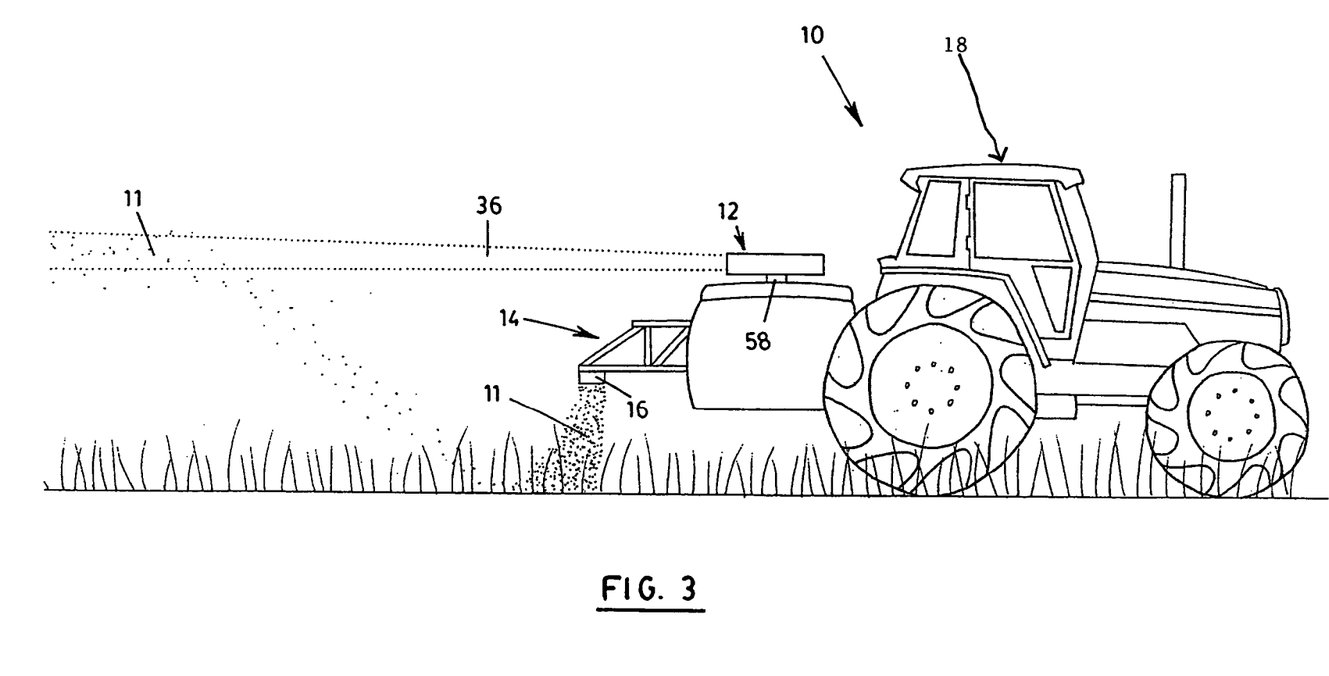
FIG. 3 is a side view of the tractor of FIG. 2.

Referring to FIGS. 1 to 3, the present invention generally provides an agricultural spraying system 10 for the controlled spraying of aerosol particles 11 over a delimited area, such as an agricultural field. This system 10 particularly includes an optical system 12 for measuring, in real-time, the spatial distribution of these aerosol particles 11, thereby determining if these particles are drifting over a sensitive area, and giving appropriate instructions to the person or automated system operating the spraying based on this measure.

The agricultural system 10 of the invention includes a vehicle 18 for circulating over the delimitated area, and a sprayer 14 mounted thereon for spraying the aerosol particles. In the illustrated embodiment the vehicle 18 is a tractor, but the present invention could equally be applied to any other appropriate vehicle apt to carry a sprayer. Such vehicles may circulate on the ground or in the air, such as an airplane. The vehicle need not be itself motorised; for example, the sprayer may be installed on a trailer pulled by another vehicle. The vehicle is operated by an operator 20, which could be a person on the vehicle or an automated system.

Throughout the present description, it is understood that the expression "sprayer" designates any device used or usable for the spraying of chemical products in aerosol form. The sprayer may include one of several nozzles 16, and may operate continuously or intermittently. The operator preferably controls the sprayer through a manual control 22, or it may alternatively be automatically operated through an automatic nozzle control 24. The sprayed aerosol may be any substance which is sprayed over an agricultural field, and is traditionally (but not exclusively) embodied by pesticides, herbicides or fertilizers.

Figure 4:
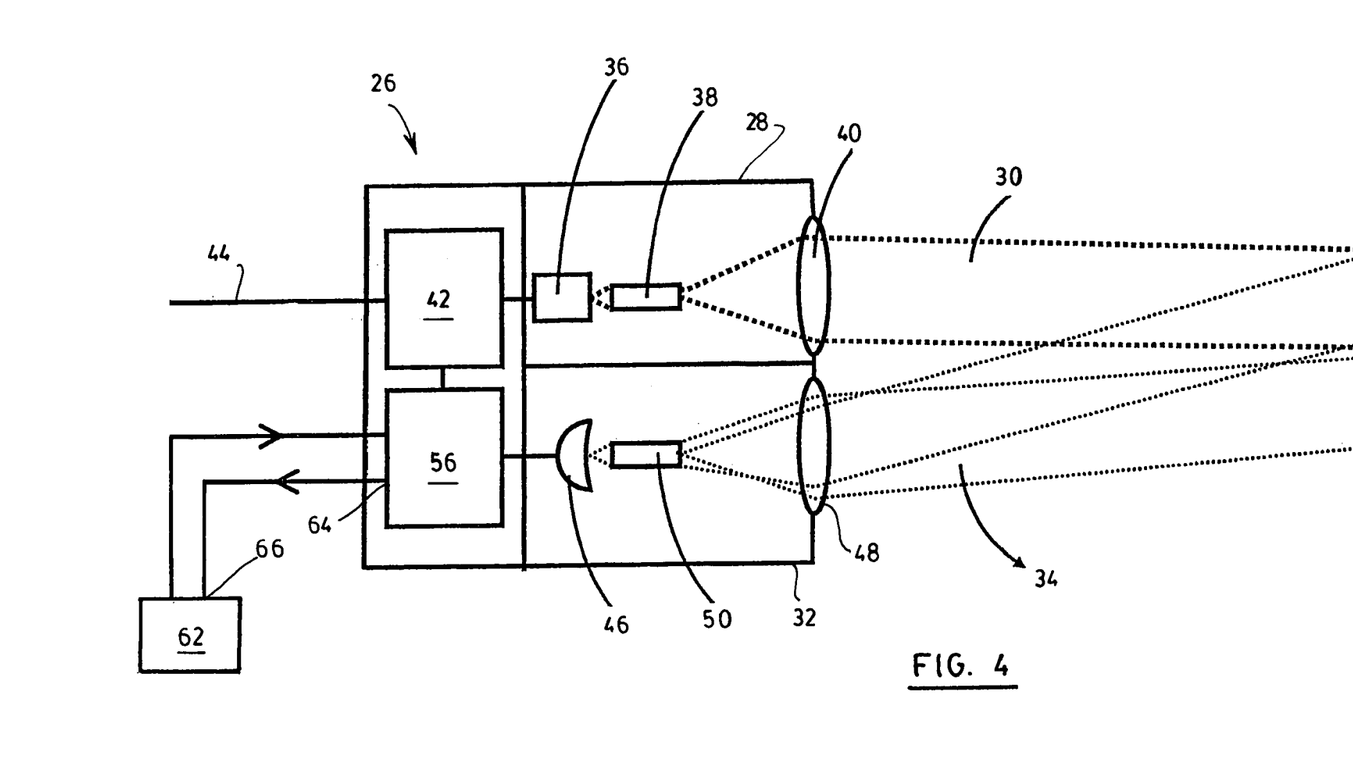
FIG. 4 is a schematical representation of an optical sensor for use in a system according to a preferred embodiment of the invention.

Referring to FIGS. 1 and 4, there is shown an optical system 12 for measuring the spatial distribution of the aerosol particles 11. The optical system 12 first includes an optical sensor 26 adapted for this measure. The sensor 26 therefore includes a light source assembly 28 which projects an excitation light beam 30 through the aerosol as it is being sprayed, and a detecting assembly 32 which detects part of the resulting scattered light 34. In the illustrated embodiment the light source assembly 28 and detecting assembly 32 are contiguous, and the detected light is therefore the back-scattered portion of all the light scattered by the particles which is within the field of view of the detecting assembly 32. The invention is however not limited to such a configuration; the light source and detecting assemblies may be oriented at any appropriate angle with respect to each other, provided an appropriate structure to secure them in this position.

The optical sensor 26 is preferably embodied by a short range LIDAR (Light Detecting And Ranging) sensor. In this particular embodiment, the excitation light beam is modulated, preferably pulsed, and is preferably generated by a pulsed laser diode or another laser source 36. The laser source 36 is controlled by a laser driver 42 powered through power supply line 44, which may advantageously be connected to the engine of the vehicle. Appropriate delivery and diffusing optics 38 shape and direct the light beam generated by the laser source to an output lens 40 which outputs the excitation light beam 30 out of the light source assembly 28.

Figure 5:
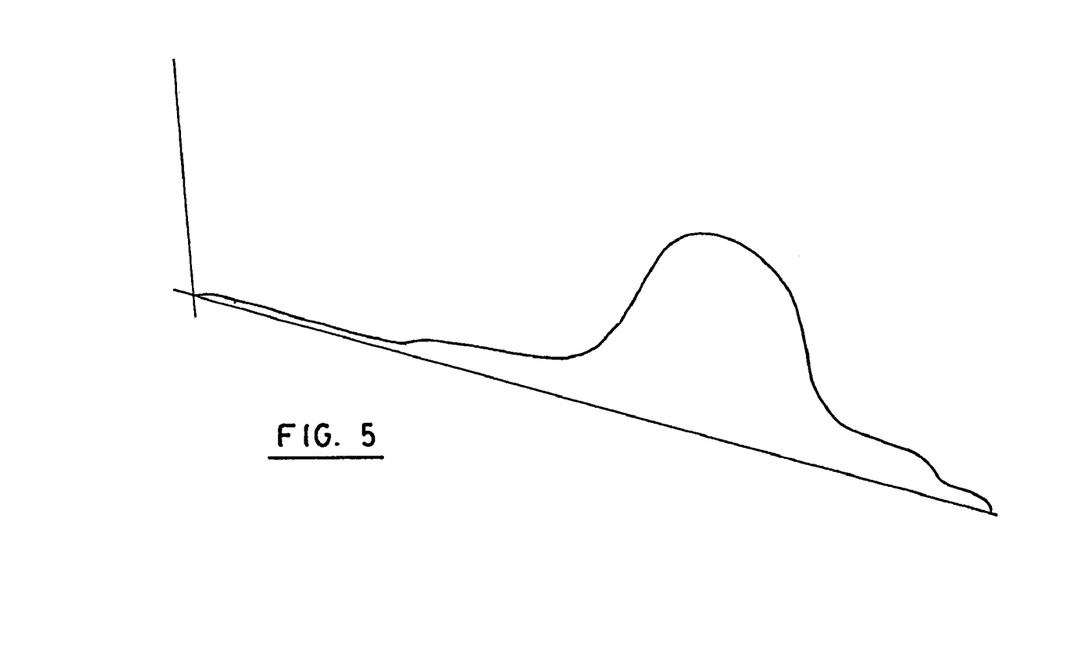
FIG. 5 schematically illustrates the information on the spatial distribution of aerosol particles obtained using the sensor of FIG. 4.

In the detecting assembly, the LIDAR sensor 26 may include a detector 46 and light-receiving optics receiving the scattered light and bringing it to this detector. The light receiving optics preferably includes an input lens 48. The detecting assembly deduces from the detected light appropriate information 49 about the spatial distribution of the particles having scattered this light. For most LIDAR system, this information 49 takes the form of an intensity value of the detected scattered light as a function of distance from the sensor, as shown in FIG. 5. An appropriate control and processing system 56 is preferably provided for this purpose. The principle of operation of a LIDAR system and the related data processing techniques are well known to one skilled in the art and need not be explained here.

The light-receiving optics preferably includes equalizing optics 50 flattening the short-range spatial response of the LIDAR sensor 26. The major impairment of using standard LIDARs for short range applications is the $1/r^2$ dependence of the signal, r being the distance from the target to the receiving optics. For short distances, like those typically considered when putting the present invention into practice, this entails a huge signal variation; a factor of 10000 (40 dB optical) between 1 m and 100 m, if all the light gathered by the receiving optics falls on the detector. It is therefore preferable to provide appropriate means to flatten the spatial response of the sensor, so that a same concentration of particles at any distance within the short operation range of the device will generate a signal of substantially the same intensity. An example of such a sensor is disclosed in the assignee's co-pending application entitled "SHORT RANGE LIDAR APPARATUS HAVING A FLAT SPATIAL RESPONSE" filed concurrently to the present application.

In the preferred embodiment, the equalization of the spatial response is accomplished by providing, as part of the equalizing optics 50, a spatial filter spatially filtering the received scattered light to obtain the desired flat spatial response. By spatially filtering, it is meant that portions of the light incident on one or more detecting planes is blocked so that only selected portions of the back scattered light is provided to the detector. These portions are selected in order for the spatial response of the apparatus to be substantially flat, that is, that a same concentration of particles at any distance within the operation range would generate a signal of substantially the same intensity.

The spatial filter may be embodied by any reflective, refractive or diffractive component or combination thereof accomplishing the desired spatial shaping of the back-scattered light. In one embodiment, the spatial filter is embodied by a mask preferably disposed in front of the detector. The mask preferably has openings therein which allow selected portions of the received scattered light therethrough. Alternatively, it may be used in reflection, in which case it may include reflecting and non-reflecting portions thereon defining the filter. In the preferred embodiment, these openings will accept all or a substantial portion of the light from the scattering volume at the far end of the operation range, for example at 50 m from the apparatus, and much less of the light from the scattering volume at 1 m or closer. The proportion of light accepted from 1 m is preferably close to 10000 times smaller than at 50 m, in order to account for the $1/r^2$ dependence.

The shape of the mask should be selected to accept the right amount of light from any scattering volume along the optical path of the excitation beam so as to render the system response as flat as possible. As will be readily understood by one skilled in the art, a great number of possible mask profiles could be used to provide the desired result. In order to design the mask, the light distributions in the plane of the mask should preferably be known for a number of reflecting surfaces along the optical path of the excitation beam. The light distributions can be deduced from simulations using optical design software or, preferably, they can be directly measured, for example with a pinhole and detector or with a digital camera. In this latter case, an appropriate optically scattering target is placed at different distances from the emitting lens. A measurement is done for each target distance, by moving the pinhole-detector pair in the mask plane or by acquiring a digital image with the camera detector in the mask plane. Once the light distribution from each target distance is known, computer software may be used to compute the spatial response for a number of different intuitively determined mask geometries until an acceptable design is found. The mask is then fabricated with an appropriate technique (such a laser micro-machining), tested and optimized.

In an alternate embodiment, instead of a mask as described above, the spatial filter may be embodied by a plurality of waveguides such as, but not limited to, optical fibers, each having an input positioned a detecting plane of the light-receiving optics and an output coupled to the detector. The inputs of the fibers are strategically distributed so as to collectively receive the appropriate portions of the received scattered light according to the principle explained above. The inputs of the optical fibers are preferably in the same detecting plane, but not necessarily. When it is the case, the fibers should all have the same length in order not to distort the time response of the system. The captured portions of the scattered light will be guided to reach the detector.

Referring to FIGS. 2 and 3, the optical sensor 12 is mounted on the vehicle itself, through any appropriate frame, platform, stage or other support 58 apt to secure the sensor in place on the vehicle. The sensor support 58 is preferably pivotable in the horizontal plane to horizontally scan the excitation light beam 30, as shown by arrow 60 on FIG. 2. The sensor support 58 may also be vertically tiltable in order to vertically align or scan the light beam 30. In an alternate embodiment (not shown), the sensor support may be fixed and a mirror or an appropriate combination of optical components can be used to move the excitation light beam horizontally, vertically or both.

Referring back to FIGS. 1 and 4, the optical system 12 according to the invention also includes a processing unit 62. The processing unit 62 is in communication with the optical sensor to receive therefrom the obtained information 49 on the spatial distribution of the particles. As mentioned above, this information 49 may include the intensity of the detected scattered light as a function of distance from the sensor. If the excitation light beam is scanning the horizontal or vertical planes, the corresponding scanning angle for each measure may also be provided to the processing unit. Any other appropriate data may of course be relayed to the processing unit by the optical sensor, such as background noise information or self-diagnostic data. The communication between the processing unit 62 and optical sensor 26 preferably goes both ways, so that the optical sensor 26 may be operated by the processing unit 62, and the exchanged data therefore serves to control power and gain of the light source, its repetition rate, adjustment to the scanning angle, etc. The processing unit may be embodied by a PC or any other appropriate computer system. In one embodiment of the invention, the processing unit 62 is provided directly aboard the vehicle. In another embodiment it is placed at a remote location, in which case the optical sensor 26 is provided with a wireless transmitter or transceiver 64, and the processing unit with a wireless receiver or transceiver 66. Preferably, the processing unit is provided with, or connected to, a data storage unit 72 for storing the information received by the processing unit 62. This advantageously provides a record of the spraying operation, which can later be used to demonstrate whether or not the sprayed aerosol has been well controlled. The data storage unit 72 may be integrated to the processing unit or be embodied by a separate device in communication therewith.

The processing unit 62 provides the operator 20 with spraying instructions based on the information received from the optical sensor. It is understood that the expression "spraying instructions" is used here to refer to any information, direction or signal given to the operator which may influence his operation of the sprayer. In a simple embodiment of the invention, the spraying instructions may simply be a warning signal 68 given the operator when it is determined that the particles are drifting, or are in danger of drifting, over a sensitive area, such as a water stream, a neighbouring field, a residential area, etc. The system preferably allow a minimal amount of particles within the sensitive area before sending the warning signal and consider that a "drift" as occurred when this amount reaches a predetermined threshold. The warning signal 68 may take any appropriate form, such as a warning light (for example a red LED turning on or flashing), or a sound alarm. In automated systems, the sprayer or vehicle may be automatically shut down.

In more complex systems, the operator may be provided with a visual representation of the spatial distribution of the particles, for example on a display showing a map of the delimited spraying area and a cloud of aerosol drifting over it. For this purpose, a GPS tracker 74 may advantageously be used to track the position of the vehicle over the field, and transmit this information to the processing unit. The agricultural spraying system of the invention may additionally be provided with one or more environmental sensors 70, sensing environmental conditions such as temperature, the humidity level, wind conditions, speed of the vehicle, etc. The collected information may be provided to the operator or stored for later reference.

The processing unit 62 may be a system dedicated to the monitoring according to the invention or a part of a more complex control or surveillance system. In cases where the sprayer 14 is operated by an automatic control 24, the processing unit 62 may provide instructions to this automated control 24. A single processing unit may also serve to monitor the spraying of aerosol from more than one vehicle at a time.

In summary, the present invention provides for a new and efficient way of monitoring the drift of aerosol particles sprayed over an agricultural field. The present invention provides a system mounted directly on the spraying vehicle which gives a clear indication of the particles' spatial distribution in real-time, allowing the operator to immediately stop or redirect the spraying operation. The preferred embodiments described above may advantageously be realised at low cost, making the invention clearly adapted for widespread use. Use of a system according to the invention may advantageously prevent the contamination of sensitive areas by pesticides or the like, as opposed to detecting it after the fact.

Of course, numerous modifications could be made to the embodiments above without departing from the scope of the present invention as defined in the appended claims.

The invention claimed is:

1. An optical system for measuring in real-time a spatial distribution of particles in an aerosol, said aerosol being sprayed from a sprayer mounted on a vehicle operated by an operator, said optical system comprising:
   a short range LIDAR optical sensor comprising a light source assembly projecting an excitation light beam through the aerosol jointly to the spraying thereof, said excitation light beam being scattered by the particles, thereby producing scattered light, said optical sensor further comprising a detecting assembly for detecting a part of said scattered light and obtain therefrom information on the spatial distribution of the particles comprising an intensity value of said detected scattered light as a function of distance from said optical sensor, said optical sensor having a substantially flat spatial response wherein a same concentration of particles at any distance within said short range will generate a signal of substantially a same intensity;

mounting means for mounting said optical sensor on the vehicle; and a processing unit in communication with the optical sensor for receiving therefrom said information on the spatial distribution of the particles said processing unit providing spraying instructions based on said information to said operator in real-time.

2. The optical system according to claim 1, wherein said mounting means comprise a sensor support pivotable in the horizontal plane for pivoting said optical sensor, thereby horizontally scanning said excitation light beam.

3. The optical system according to claim 2, wherein said sensor support is vertically tiltable for vertically moving said excitation light beam.

4. The optical system according to claim 1, wherein said detecting assembly is positioned contiguously to said light source assembly in order to detect a back-scattered portion of said scattered light.

5. The optical system according to claim 1, wherein said processing unit is located aboard said vehicle.

6. The optical system according to claim 1, wherein said processing unit is at a location remote from said vehicle, and wherein:

said optical sensor is provided with a wireless transmitter for transmitting said information; and said processing unit is provided with a wireless receiver for receiving said information.

7. The optical system according to claim 1, wherein said light source assembly comprises a pulsed laser source generating said excitation light beam.

8. The optical system according to claim 7, wherein said detector assembly comprises a detector and light-receiving optics receiving the part of the scattered light.

9. The optical system according to claim 1, wherein said detecting assembly further comprises a spatial filter spatially filtering said part of the scattered light so as to flatten said spatial response of the optical sensor.

10. The optical system according to claim 1, wherein said spraying instructions comprise a warning signal provided to said operator when said information indicates a drift of the particles in a sensitive area.

11. The optical system according to claim 1, wherein said spraying instructions comprise a visual representation of the spatial distribution of the particles.

12. The optical system according to claim 1, further comprising a data storage unit for storing said information received by the processing unit.

13. An agricultural spraying system for the controlled spraying of aerosol particles over a delimited area, comprising:

a vehicle for circulating over said delimited area, said vehicle being operated by an operator;

a sprayer, mounted on said vehicle, for spraying said aerosol particles as said vehicle circulates over said delimited area; and an optical system for measuring in real-time a spatial distribution of said particles, comprising:

a short range LIDAR optical sensor comprising a light source assembly projecting an excitation light beam through the aerosol jointly to the spraying thereof, said excitation light beam being scattered by the particles, thereby producing scattered light, said optical sensor further comprising a detecting assembly for detecting a part of said scattered light and obtain therefrom information on the spatial distribution of the particles comprising an intensity value of said detected scattered light as a function of distance from said optical sensor, said optical sensor having a substantially flat spatial response wherein a same concentration of particles at any distance within said short range will generate a signal of substantially a same intensity;

mounting means for mounting said optical sensor on the vehicle; and a processing unit in communication with the optical sensor for receiving therefrom said information on the spatial distribution of the particles, said processing unit providing spraying instructions based on said information to said operator in real-time.

14. The agricultural spraying system according to claim 13, wherein said vehicle is a tractor.

15. The agricultural spraying system according to claim 13, wherein said sprayer comprises a plurality of nozzles.

16. The agricultural spraying system according to claim 13, wherein said operator is a person driving said vehicle.

17. The agricultural spraying system according to claim 13, wherein said operator is an automated system controlling said vehicle.

18. The agricultural spraying system according to claim 13, wherein said aerosol particles are selected from the group consisting of pesticides, herbicides and fertilizers.

19. The agricultural spraying system according to claim 13, wherein said mounting means comprise a sensor support pivotable in the horizontal plane for pivoting said optical sensor, thereby horizontally scanning said excitation light beam.

20. The agricultural spraying system according to claim 19, wherein said sensor support is vertically tiltable for vertically moving said excitation light beam.

21. The agricultural spraying system according to claim 13, wherein said detecting assembly is positioned contiguously to said light source assembly in order to detect a back-scattered portion of said scattered light.

22. The agricultural spraying system according to claim 13, wherein said processing unit is located aboard said vehicle.

23. The agricultural spraying system according to claim 13, wherein said processing unit is at a location remote from said vehicle, and wherein:

said optical sensor is provided with a wireless transmitter for transmitting said information; and said processing unit is provided with a wireless receiver for receiving said information.

24. The agricultural spraying system according to claim 13, wherein said spraying instructions comprise a warning signal provided to said operator when said information indicates a drift of the particles in a sensitive area.

25. The agricultural spraying system according to claim 13, wherein said spraying instructions comprise a visual representation of the spatial distribution of the particles.

26. The agricultural spraying system according to claim 13, further comprising a data storage unit for storing said information received by the processing unit.

27. The agricultural spraying system according to claim 13, further comprising at least one environmental sensor for sensing environmental conditions of said spraying, said at least one environmental sensor providing said environmental conditions to the processing unit.

28. The agricultural spraying system according to claim 27, wherein said environmental conditions are selected from the group comprising a temperature, a humidity level, wind conditions, and a speed of the vehicle.

29. The agricultural spraying system according to claim 13, further comprising a GPS sensor tracking a position of the vehicle over said delimited area, said GPS sensor being in communication with the processing unit.

30. The agricultural spraying system according to claim 29, wherein said processing unit correlates the position of the vehicle tracked by the GPS sensor with the information on the spatial distribution of the particles to obtain an actual position of the aerosol with respect to said delimited area.

* * * * *